US012654007B1

(12) United States Patent
Imanuel et al.

(10) Patent No.: US 12,654,007 B1
(45) Date of Patent: Jun. 16, 2026

(54) SYSTEMS AND METHODS FOR DETERMINING TRANSDUCER LOCATIONS FOR DELIVERING TUMOR TREATING FIELDS USING AN INITIAL ESTIMATE

(71) Applicant: Novocure GmbH, Root (CH)

(72) Inventors: Ido Imanuel, Haifa (IL); Yissachar Abraham, Haifa (IL); Amit Feldman, Haifa (IL)

(73) Assignee: Novocure GmbH, Baar (CH)

( * ) Notice: Subject to any disclaimer, the term of this patent is extended or adjusted under 35 U.S.C. 154(b) by 280 days.

(21) Appl. No.: 18/513,290

(22) Filed: Nov. 17, 2023

Related U.S. Application Data

(60) Provisional application No. 63/442,193, filed on Jan. 31, 2023, provisional application No. 63/426,467, filed on Nov. 18, 2022.

(51) Int. Cl.
$A61N\ 1/36$ (2006.01)
$A61N\ 1/02$ (2006.01)
$A61N\ 1/04$ (2006.01)

(52) U.S. Cl.
CPC ......... *A61N 1/36002* (2017.08); *A61N 1/025* (2013.01); *A61N 1/0476* (2013.01); *A61N 1/36034* (2017.08)

(58) Field of Classification Search
None
See application file for complete search history.

(56) References Cited

U.S. PATENT DOCUMENTS

| | | | |
|---|---|---|---|
| 7,565,205 B2 | 7/2009 | Palti | |
| 2016/0228702 A1* | 8/2016 | Kempe | A61N 1/0476 |
| 2017/0120041 A1* | 5/2017 | Wenger | A61B 5/055 |
| 2021/0196943 A1* | 7/2021 | Shamir | G16H 20/30 |
| 2022/0313992 A1* | 10/2022 | Wasserman | A61N 1/0476 |

* cited by examiner

*Primary Examiner* — Michael W Kahelin
(74) *Attorney, Agent, or Firm* — McCarter & English, LLP; Michael A. Sartori

(57) ABSTRACT

A computer-implemented method for selecting at least one transducer location for delivering TTFields to a subject, the method including: obtaining a three-dimensional model of the subject, the model including voxels; computing an initial vector $\phi'$ for each of a plurality of transducer locations, wherein each initial vector $\phi'$ represents an initial estimate of electrical potentials for the model for each respective transducer location; computing a matrix A and a vector b, wherein the matrix A is based on the model, wherein the vector b is based on boundary conditions for each respective transducer location; computing a vector $\phi$ using the matrix A, the vector b, and the initial vector $\phi'$ for each transducer location, wherein $A\phi=b$, wherein each vector $\phi$ represents electrical potentials for the model for each respective transducer location; and selecting transducer location(s) for delivering tumor treating fields to the subject based on the vectors $\phi$.

20 Claims, 7 Drawing Sheets

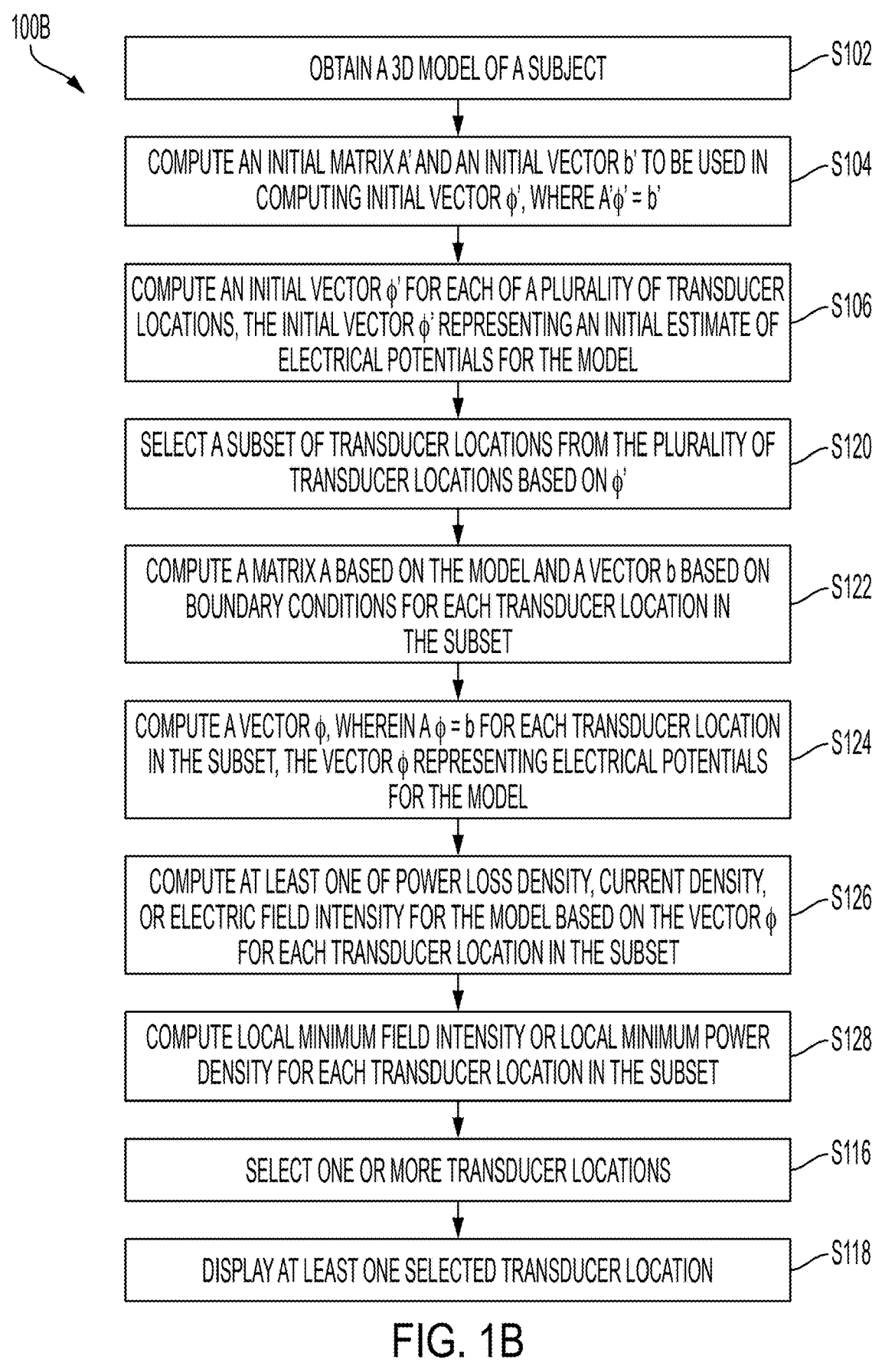

100B

| |
|---|
| OBTAIN A 3D MODEL OF A SUBJECT — S102 |

↓

| |
|---|
| COMPUTE AN INITIAL MATRIX A' AND AN INITIAL VECTOR b' TO BE USED IN COMPUTING INITIAL VECTOR φ', WHERE A'φ' = b' — S104 |

↓

| |
|---|
| COMPUTE AN INITIAL VECTOR φ' FOR EACH OF A PLURALITY OF TRANSDUCER LOCATIONS, THE INITIAL VECTOR φ' REPRESENTING AN INITIAL ESTIMATE OF ELECTRICAL POTENTIALS FOR THE MODEL — S106 |

↓

| |
|---|
| SELECT A SUBSET OF TRANSDUCER LOCATIONS FROM THE PLURALITY OF TRANSDUCER LOCATIONS BASED ON φ' — S120 |

↓

| |
|---|
| COMPUTE A MATRIX A BASED ON THE MODEL AND A VECTOR b BASED ON BOUNDARY CONDITIONS FOR EACH TRANSDUCER LOCATION IN THE SUBSET — S122 |

↓

| |
|---|
| COMPUTE A VECTOR φ, WHEREIN A φ = b FOR EACH TRANSDUCER LOCATION IN THE SUBSET, THE VECTOR φ REPRESENTING ELECTRICAL POTENTIALS FOR THE MODEL — S124 |

↓

| |
|---|
| COMPUTE AT LEAST ONE OF POWER LOSS DENSITY, CURRENT DENSITY, OR ELECTRIC FIELD INTENSITY FOR THE MODEL BASED ON THE VECTOR φ FOR EACH TRANSDUCER LOCATION IN THE SUBSET — S126 |

↓

| |
|---|
| COMPUTE LOCAL MINIMUM FIELD INTENSITY OR LOCAL MINIMUM POWER DENSITY FOR EACH TRANSDUCER LOCATION IN THE SUBSET — S128 |

↓

| |
|---|
| SELECT ONE OR MORE TRANSDUCER LOCATIONS — S116 |

↓

| |
|---|
| DISPLAY AT LEAST ONE SELECTED TRANSDUCER LOCATION — S118 |

FIG. 1B

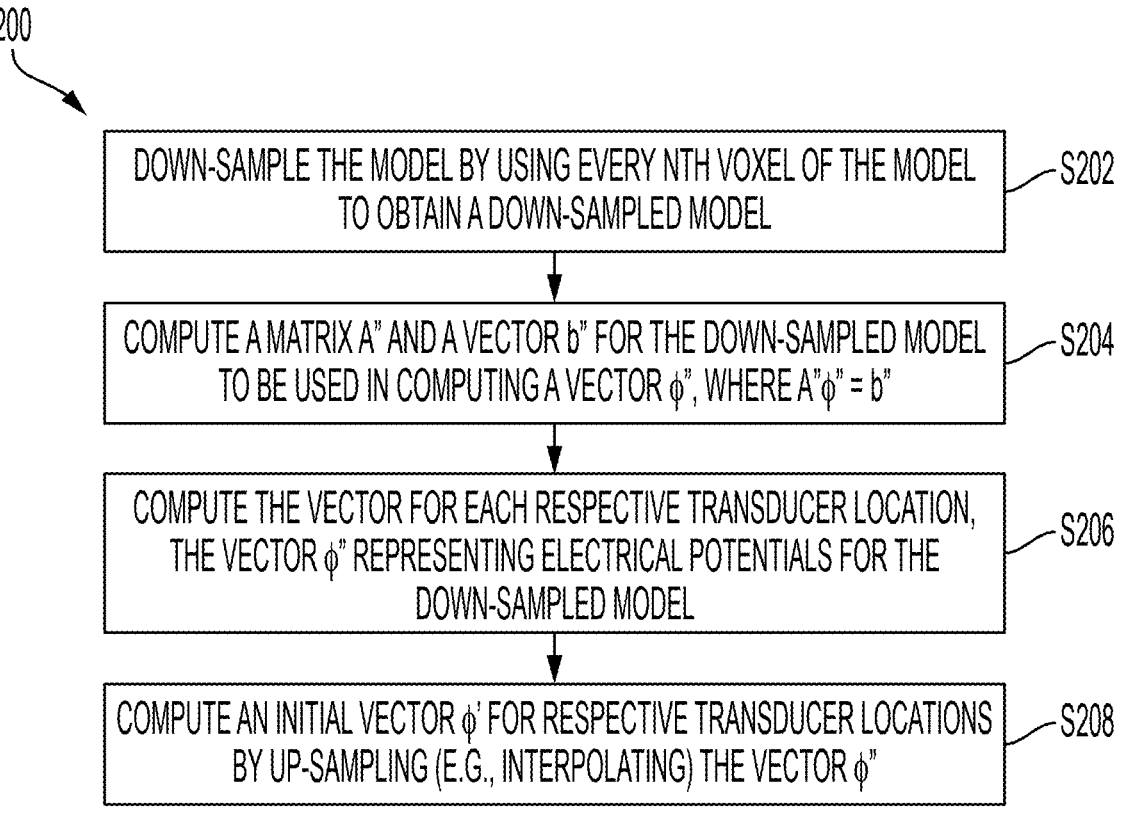

200

DOWN-SAMPLE THE MODEL BY USING EVERY NTH VOXEL OF THE MODEL
TO OBTAIN A DOWN-SAMPLED MODEL — S202

COMPUTE A MATRIX A" AND A VECTOR b" FOR THE DOWN-SAMPLED MODEL
TO BE USED IN COMPUTING A VECTOR $\phi$", WHERE A"$\phi$" = b" — S204

COMPUTE THE VECTOR FOR EACH RESPECTIVE TRANSDUCER LOCATION,
THE VECTOR $\phi$" REPRESENTING ELECTRICAL POTENTIALS FOR THE
DOWN-SAMPLED MODEL — S206

COMPUTE AN INITIAL VECTOR $\phi$' FOR RESPECTIVE TRANSDUCER LOCATIONS
BY UP-SAMPLING (E.G., INTERPOLATING) THE VECTOR $\phi$" — S208

FIG. 2

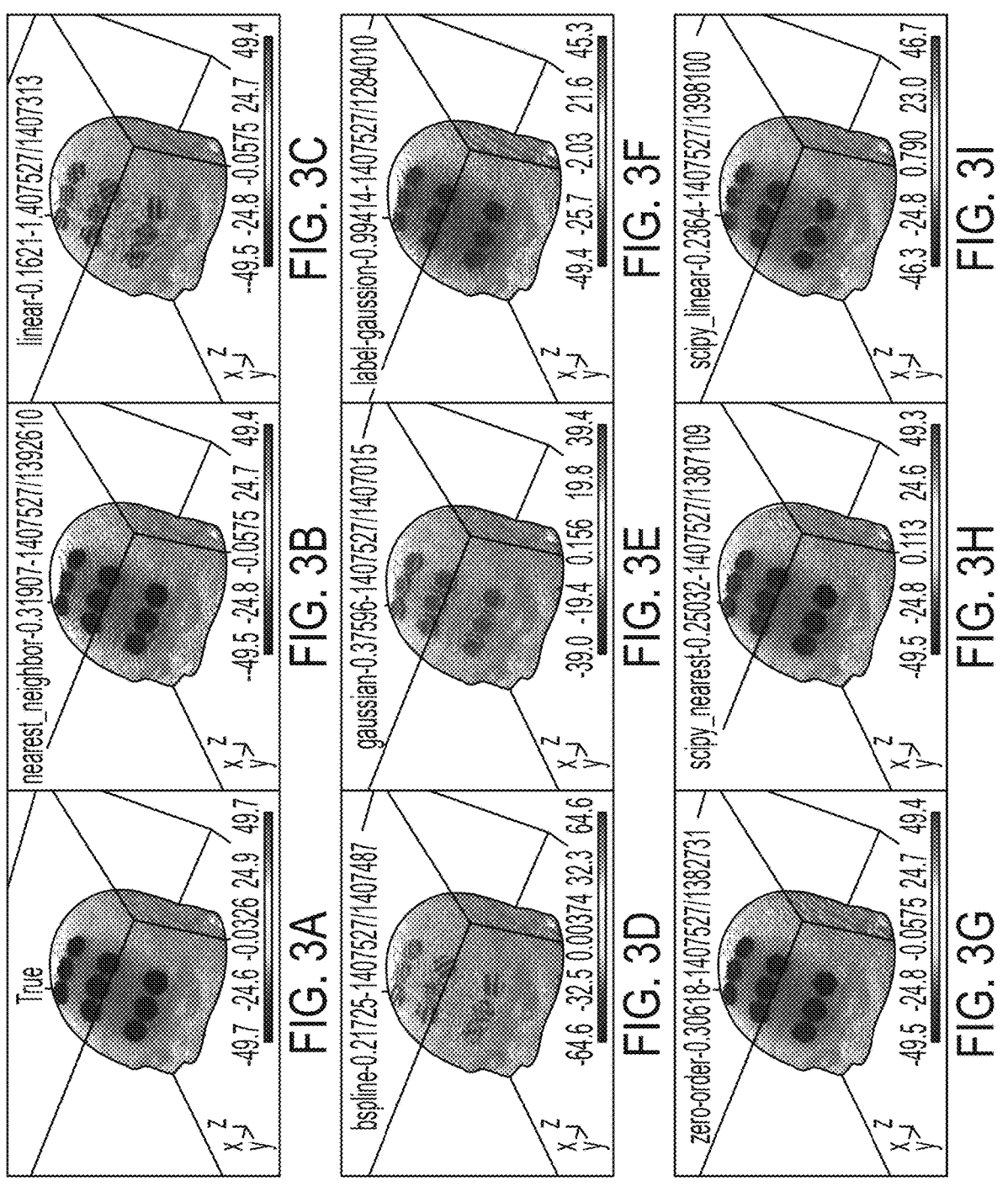

Figures 4A, 4B, 5A, 5B:
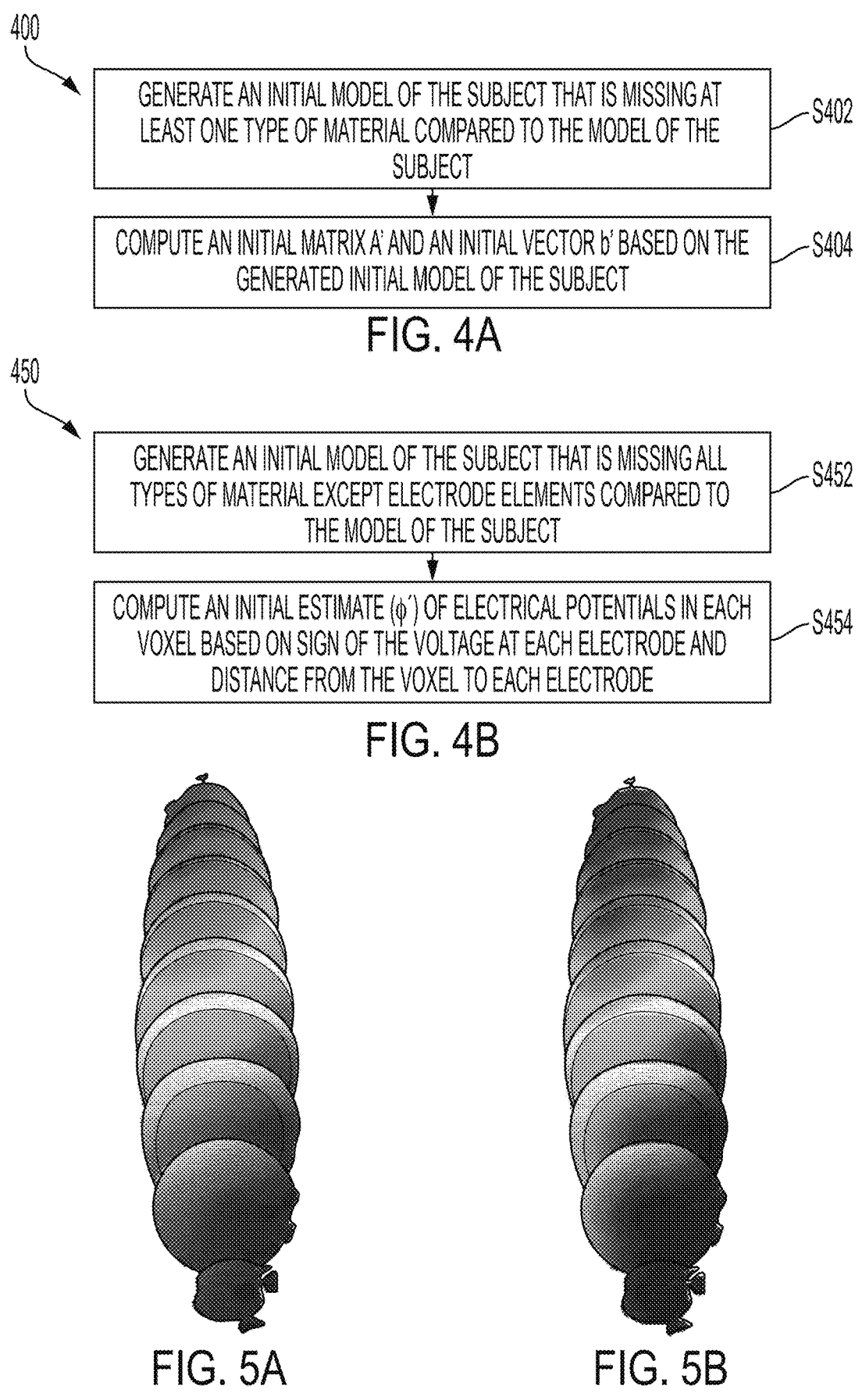

400

| GENERATE AN INITIAL MODEL OF THE SUBJECT THAT IS MISSING AT LEAST ONE TYPE OF MATERIAL COMPARED TO THE MODEL OF THE SUBJECT | S402 |

| COMPUTE AN INITIAL MATRIX A' AND AN INITIAL VECTOR b' BASED ON THE GENERATED INITIAL MODEL OF THE SUBJECT | S404 |

| GENERATE AN INITIAL MODEL OF THE SUBJECT THAT IS MISSING ALL TYPES OF MATERIAL EXCEPT ELECTRODE ELEMENTS COMPARED TO THE MODEL OF THE SUBJECT | S452 |

| COMPUTE AN INITIAL ESTIMATE ($\phi'$) OF ELECTRICAL POTENTIALS IN EACH VOXEL BASED ON SIGN OF THE VOLTAGE AT EACH ELECTRODE AND DISTANCE FROM THE VOXEL TO EACH ELECTRODE | S454 |

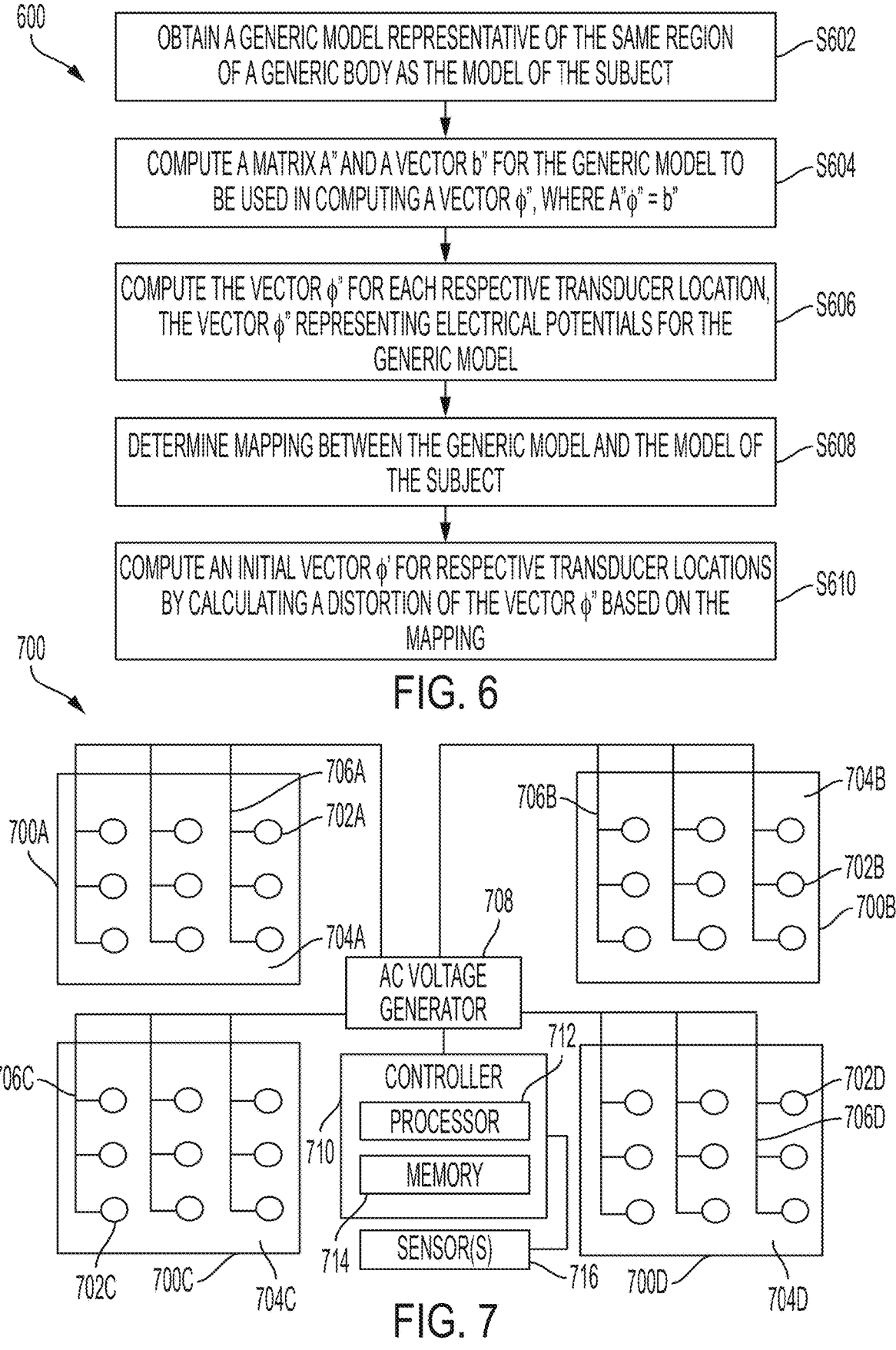

600

| S602 | OBTAIN A GENERIC MODEL REPRESENTATIVE OF THE SAME REGION OF A GENERIC BODY AS THE MODEL OF THE SUBJECT |

COMPUTE A MATRIX A" AND A VECTOR b" FOR THE GENERIC MODEL TO BE USED IN COMPUTING A VECTOR φ", WHERE A"φ" = b" — S604

COMPUTE THE VECTOR φ" FOR EACH RESPECTIVE TRANSDUCER LOCATION, THE VECTOR φ" REPRESENTING ELECTRICAL POTENTIALS FOR THE GENERIC MODEL — S606

DETERMINE MAPPING BETWEEN THE GENERIC MODEL AND THE MODEL OF THE SUBJECT — S608

COMPUTE AN INITIAL VECTOR φ' FOR RESPECTIVE TRANSDUCER LOCATIONS BY CALCULATING A DISTORTION OF THE VECTOR φ" BASED ON THE MAPPING — S610

AC VOLTAGE GENERATOR
708

706C
700C
702C
704C

CONTROLLER
712
710
PROCESSOR
714
MEMORY
SENSOR(S)
716

SYSTEMS AND METHODS FOR DETERMINING TRANSDUCER LOCATIONS FOR DELIVERING TUMOR TREATING FIELDS USING AN INITIAL ESTIMATE

CROSS-REFERENCE TO RELATED APPLICATIONS

This application claims priority to U.S. Provisional Application No. 63/426,467, filed Nov. 18, 2022, and U.S. Provisional Application No. 63/442,193, filed Jan. 31, 2023, the content of which are incorporated by reference herein in their entirety.

BACKGROUND

Tumor treating fields (TTFields) are low intensity alternating electric fields within the intermediate frequency range (for example, 50 kHz to 1 MHz), which may be used to treat tumors as described in U.S. Pat. No. 7,565,205. TTFields are induced non-invasively into a region of interest by transducers placed on the patient's body and applying alternating current (AC) voltages between the transducers. Conventionally, a first pair of transducers and a second pair of transducers are placed on the subject's body. AC voltage is applied between the first pair of transducers for a first interval of time to generate an electric field with field lines generally running in the front-back direction. Then, AC voltage is applied at the same frequency between the second pair of transducers for a second interval of time to generate an electric field with field lines generally running in the right-left direction. The system then repeats this two-step sequence throughout the treatment.

BRIEF DESCRIPTION OF THE DRAWINGS

FIGS. 1A and 1B depict example methods of selecting transducer locations for delivering TTFields to a subject.

FIG. 2 depicts an example method of computing an initial estimate using down-sampling.

FIGS. 3A-3I depict example simulation results using various interpolation schemes.

FIG. 4A depicts an example method of computing an initial estimate using a model of the subject that is missing at least one type of material. FIG. 4B depicts an example method of computing an initial estimate using a model of the subject that is missing all types of material except for electrode elements.

FIGS. 5A and 5B depict example simulation results of electrical potentials in a model.

FIG. 6 depicts an example method of computing an initial estimate using a generic model.

FIG. 7 depicts an example system for delivering TTFields to a subject's body.

DESCRIPTION OF EMBODIMENTS

Figure 1A:
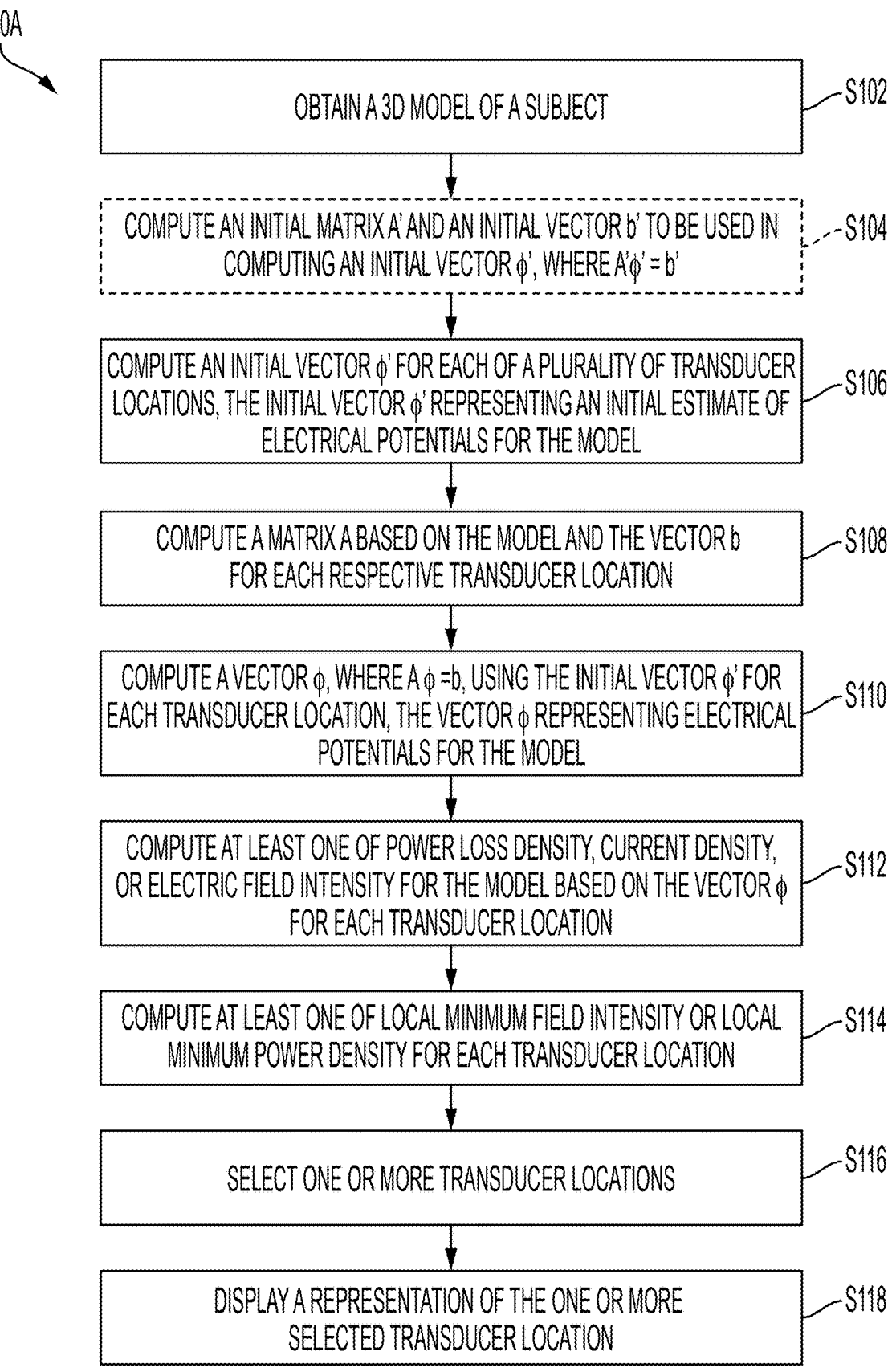

This application describes exemplary techniques to computationally determine where to place transducers on a subject.

In general, one or more pairs of transducers are positioned on the subject's body and used to alternately apply TTFields to the subject's body. Generally, it is preferred that there are at least two pairs of transducers. Transducers used to apply TTFields to a subject's body often include multiple electrode elements coupled together on a substrate. Determining where to place the transducers on the subject involves using very large data sets and computationally solving complex algorithms. The computations may take a significant amount of time, especially since multiple transducer locations are simulated to determine one or more transducer locations to recommend to achieve an appropriate dosage of the TTFields.

The inventors discovered computational techniques to vastly reduce the computation time needed to solve the complex algorithms and to recommend the one or more transducer locations. The inventive techniques are particularly integrated into a practical application. With the inventive techniques, more transducer locations may be simulated much quicker than previous techniques. With the inventive techniques, simulations for more patients may be performed compared to previous techniques. In addition, a selection of the preferred transducer location(s) may be made from a much greater number of potential transducer locations than is possible in the same amount of time using previous techniques. This may result in improved TTFields treatment efficacy (dosage applied to a region of interest) in the same computational time, since more potential locations are considered in the analysis.

In particular, the inventors discovered computational techniques that include determining an initial estimate for solving the complex algorithms, which thereby reduces the computational time. The disclosed techniques allow less time to be spent determining the solution to an iterative optimization by first solving a simpler (e.g., approximate) problem that is particular to the subject, then inputting this solution as an initial estimate into the complex optimization algorithm. This provides a "warm start" to the optimization algorithm, compared to previous techniques which start the optimization algorithm with a standard initial guess. As such, the system described in this disclosure provides a practical application to perform a larger number of iterative optimization processes and/or a same number of iterative optimization processes in less computational time by determining and inputting subject-specific initial estimates to determine and select one or more transducer locations on a subject's body. In some embodiments, the discovered computational techniques lead to the technical advantages of processing a three-dimensional model of a subject based on magnetic resonance imaging (MRI) scans of the subject to efficiently reduce the computational time needed to determine where to place transducers on the subject to deliver corresponding TTFields dosages to the subject.

FIGS. 1A and 1B depict example computer-implemented methods 100A and 100B for selecting at least one transducer location for delivering TTFields to a subject. For each of FIGS. 1A/1B, the method 100A/100B may be implemented by a computer, the computer including one or more processors and memory accessible by the one or more processors, the memory storing instructions that when executed by the one or more processors cause the computer to perform the steps of the method 100A/100B. Modifications, additions, or omissions may be made to method 100A/100B. While an order of operations is indicated in FIGS. 1A/1B for illustrative purposes, the timing and ordering of such operations may vary where appropriate without negating the purpose and advantages of the examples set forth in detail herein.

The method 100A includes, at step S102, obtaining a three-dimensional (3D) model of the subject. The model includes voxels. Each voxel of the model may be assigned a type of tissue (e.g., bone, organs, fluid, skin, or tumor) and/or an electrical conductivity associated with the type of tissue. As an example, the model of the subject may represent a head of the subject. As an example, the model of the subject may represent a torso of the subject. Other body parts of the subject may be represented in the model of the subject in other embodiments.

The model may be obtained using image data, for example, via a computer identifying the different types of tissue from the image data. The image data may include one or more images of a portion of the subject's body (e.g., X-ray images, MRI images, computerized tomography (CT) images, ultrasound images, or any image providing an internal view of the subject's body). Each medical image may include an outer shape of a portion of the subject and a region corresponding to the region of interest (e.g., tumor) within the subject. The 3D model may be obtained, for example, from computer memory locally or over a network.

At step S104, the method 100A may optionally include computing an initial matrix A' and an initial vector b' to be used in computing an initial vector φ'. The initial matrix A' may represent one or more types of tissue, estimated tissue conductivity, and/or other features located in the voxels of an initial model of the subject's body. This "initial model" may be different than but related to the model of the subject's body obtained in step S102. For example, the initial model represented by initial matrix A' may be a down-sampled version of the model of the subject, a model of the subject with one or more types of material removed (e.g., a model with all tissue, ceramic, polymer, gel, and any other materials that are not perfect conductors removed), or others.

The initial vector b' may be computed based on boundary conditions for each of a plurality of transducer locations. The initial vector b' may represent the boundary conditions at each transducer location within the initial model of the subject's body, and these transducer locations correspond to possible locations for placement of transducers on the subject's body.

The term "transducer location" used herein may include more than one location. For example, each "transducer location" may include locations for two pairs of transducers. In such instances, a first pair of the two pairs of transducers has a first transducer and a second transducer located on opposite sides of the subject. Similarly, a second pair of the two pairs of transducers has a third transducer and a fourth transducer located on opposite sides of the subject. Each transducer location may include locations for at least two transducer arrays, with each transducer array including a plurality of electrode elements. The electrode elements on a transducer array may be capacitively coupled or may not be capacitively coupled. The electrode elements on a transducer array may be polymer films or ceramic disks or may take other forms.

At step S106, the method 100A includes computing an initial vector φ' for each of the plurality of transducer locations. Each initial vector φ' represents an initial estimate of electrical potentials for the model for a respective transducer location. This initial vector φ' may be input to an iterative optimizer, as discussed below.

In some embodiments, the initial vector φ' for each transducer location may be computed using the initial matrix A' and the initial vector b' (computed in step S104) for each transducer location. Specifically, the initial vector φ' may be computed by solving the system of linear equations (1):

$$A'\phi'=b' \tag{1}$$

In other embodiments, the initial vector φ' may be computed using other methods, for example, such as those discussed in detail below.

At step S108, the method 100A includes computing a matrix A and a vector b. The matrix A may be computed based on one or more types of tissue, tissue conductivity, boundary conditions such as voltage values, and/or other features located in each voxel of the model of the subject's body obtained in step S102. The matrix A may be computed based on the model of the subject. Each vector b may be computed based on one or more types of tissue, tissue conductivity, and/or the boundary conditions for each respective transducer location of a plurality of transducer locations. In particular, each vector b may represent the boundary conditions at one of multiple transducer locations within the model of the subject's body. These are the transducer locations from which at least one transducer location will be selected in the method 100A. The boundary conditions may represent the transducer locations as voltage sources on the subject, the transducer locations as current sources on the subject, and/or surface conditions such as a Neumann boundary condition on the surface of the subject.

At step S110, the method 100A includes computing a vector φ using the matrix A, the vector b, and the initial vector φ' for each transducer location. The vector φ may be computed by computationally solving the system of linear equations (2):

$$A\phi=b \tag{2}$$

Each vector φ represents electrical potentials for the model for each respective transducer location. Equation (2) may be solved using an iterative optimizer with the initial vector φ' input as an initial estimate for the vector φ, for each transducer location. The iterative optimizer may be a linear equation solver or an algebraic multigrid (AMG) linear solver. Other types of iterative optimizers may be used without departing from the scope of the present disclosure.

At step S112, the method 100A may include computing at least one of electric power loss density, current density, or electric field intensity at locations of the model of the subject using the vector φ for each transducer location. These may be the electric power loss density, current density, or electric field intensity at a region of interest (e.g., representing a tumor) within the model. A higher electric power loss density, current density, or electric field intensity in the region of interest may be desired, as this indicates application of a higher dose of TTFields to the region of interest.

As such, the method 100A may be used to compute a dosage of TTFields delivered to the subject. The dosage may be computed based on at least one of the computed electric power loss density, computed current density, or computed electric field intensity of step S112.

At step S114, the method 100A may include computing at least one of local minimum field intensity (LMiFI) or local minimum power density (LMiPD). The LMiFI or LMiPD may represent the minimum dose delivered by the TTFields to a region of interest (e.g., tumor) via the particular transducer layout. The LMiFI and/or LMiPD may be used to compute an estimated dosage of TTFields that will be delivered to the subject via transducers positioned at the locations corresponding to the vector φ. In some embodiments, the dosage is at least one of the computed LMiFI or computed LMiPD. A higher LMiFI or LMiPD in the region of interest may be desired, as this indicates application of a higher dose of TTFields to the region of interest.

At step S116, the method 100A includes selecting one or more transducer locations for delivering TTFields to the subject. In some embodiments, the one or more transducer locations are selected based on the computed electric power loss density, computed current density, and/or computed electric field intensity from step S112. In particular, the transducer location corresponding to the vector φ associated with the highest computed electric power loss density, the highest computed current density, and/or the highest computed electric field intensity may be selected. In some embodiments, the one or more transducer locations may be selected based on the computed LMiFI or computed LMiPD of step S114. For example, the transducer location corresponding to the vector φ associated with the highest computed LMiFI or LMiPD may be selected.

At step S118, the method 100A may include displaying a representation of the one or more selected transducer locations on a representation of the subject. In some embodiments, step S118 may include displaying at least two selected transducer locations.

In FIG. 1B, the method 100B may include the same steps S102-S106, S116, and S118 as described above with reference to the method 100A of FIG. 1A.

At step S120, the method 100B includes selecting a subset of transducer locations from the plurality of transducer locations for further processing, based on the computed initial vectors φ'. The subset of transducer locations may include the transducer locations for which the corresponding initial vector φ' indicates a higher estimated dosage of TTFields applied to a region of interest. For example, the subset of transducer locations may be selected based on which vectors φ' indicate electrical potentials over a predetermined threshold.

At step S122, the method 100B includes computing a matrix A and a vector b for each transducer location in the subset.

At step S124, the method 100B includes computing a vector φ using the matrix A and the vector b (wherein Aφ=b) for each transducer location in the subset. Computation of the vector φ using the matrix A and the vector b may be performed using the corresponding initial vector φ' as a starting point in an iterative optimization, or not.

Steps S126 and S128 are similar to steps S112 and S114 of FIG. 1A, respectively, except that steps S126 and S128 are only performed for the transducers in the subset of transducers selected in step S120 (as opposed to each transducer of the original plurality). As such, the initial vectors φ' may be evaluated and used to narrow down the number of transducer locations for which the final solution to Aφ=b will be computed, reducing computational time.

FIG. 2 depicts an example method 200 for computing an initial estimate (e.g., initial vector φ') for each transducer location based on a down-sampled model of the subject. This example method 200 may be used to accomplish step S106 in the method 100A/100B of FIG. 1A/1B. The method 100A/100B of FIG. 1A/1B may not include step S104 when the method 200 is used for step S106. While an order of operations is indicated in FIG. 2 for illustrative purposes, the timing and ordering of such operations may vary where appropriate without negating the purpose and advantages of the examples set forth in detail herein.

At step S202, the method 200 includes down-sampling the model of the subject's body obtained at S102 to obtain a down-sampled model. As an example, the model of the subject's body may be down-sampled (S202) by using every $n^{th}$ voxel of the model (e.g., taking the model from 256× 256×256 voxels to 128×128×128 voxels for n=2).

At step S204, the method 200 may include computing a matrix A″ and a vector b″ for the down-sampled model to be used in computing a vector φ″. The matrix A″ may represent one or more types of tissue, estimated tissue conductivity, and/or other features located in the voxels of the down-sampled model. The vector b″ may represent boundary conditions within the down-sampled model and may be computed based on boundary conditions for a respective transducer location.

At step S206, the method 200 may include computing the vector φ″ for each respective transducer location. Specifically, the vector φ″ for each transducer location may be computed by computationally solving the system of linear equations (3):

$$A''\phi''=b'' \qquad (3)$$

At step S208, the method 200 may include computing the initial vector φ' for each respective transducer location by up-sampling the vector φ″ computed in step S206. The up-sampling of the vector φ″ involves interpolating the values of the vector φ″ back to the size of a vector φ corresponding to the full size of the model of the subject's body. That is, the vector φ″ for the down-sampled model is interpolated to provide an initial vector φ' sized for the model of the subject's body. The vector φ″ may be up-sampled by interpolating the vector φ″ using one of nearest neighbor interpolation, linear interpolation, b-spline interpolation, Gaussian interpolation, label Gaussian interpolation, zero order interpolation, SciPy nearest interpolation, SciPy linear interpolation, or quadratic interpolation.

By first solving for the initial vector φ' using the simplified, down-sampled model, the method 200 provides a closer initial estimate for input to the optimization algorithm, thereby reducing the total amount of time to solve for $ and select one or more transducer locations.

FIGS. 3A-3I depict results of different simulations showing the electrical potentials at a transducer location on a subject's head. FIG. 3A depicts a simulation of the electrical potentials (φ) computed by solving Equation (2), without down-sampling the model. This represents the results, for example, of step S110 of FIG. 1A but with an initial estimate for the initial vector φ' using a previous technique. FIGS. 3B-3I depict different simulations of the electrical potentials (§ ') computed by up-sampling the vector φ″ computed in Equation (3). FIGS. 3B-3I represent the results, for example, of step S106 of FIG. 1A. The simulation results shown in FIGS. 3B-3I each represent an initial vector φ' (initial estimate) to be used to solve Equation (2) and reach the results of FIG. 3A more quickly.

Each of FIGS. 3B-3I depicts a simulation resulting from a computation of the initial vector φ' that used the same vector φ″ but a different interpolation scheme for up-sampling (e.g., step S208 of FIG. 2). In FIGS. 3B-3I, the up-sampling was performed by interpolating the vector φ″ using, for FIG. 3B: nearest neighbor interpolation; for FIG. 3C: linear interpolation; for FIG. 3D: b-spline interpolation; for FIG. 3E: Gaussian interpolation; for FIG. 3F: label Gaussian interpolation; for FIG. 3G: zero order interpolation; for FIG. 3H: SciPy nearest interpolation; and for FIG. 3I: SciPy linear interpolation.

FIG. 4A depicts an example method 400 for computing an initial estimate (e.g., initial vector φ') for each transducer location based on an initial model of the subject that is missing at least one type of material compared to the model of the subject. This example method 400 may be used to accomplish step S104 in the method 100A/100B of FIG. 1A/1B. While an order of operations is indicated in FIG. 4A for illustrative purposes, the timing and ordering of such operations may vary where appropriate without negating the purpose and advantages of the examples set forth in detail herein.

At step S402, the method 400 may include generating an initial model of the subject that is missing at least one type of material compared to the model of the subject. That is, the initial model may be generated by taking the model of the subject's body and changing the values in voxels associated with the at least one type of material to be removed to zero (or another values that signifies a lack of material at the voxel locations). As such, generating the initial model may include removing all instances of the at least one type of material from the voxels of the model of the subject's body. The initial model of the subject may be missing, for example, brain tissue compared to the model of the subject. Other, or additional, types of tissue or other material(s) may also be missing from the initial model in other embodiments. The initial model may be generated based on an assumption of a uniform medium (e.g., air) and/or a lack of material located throughout the voxels representative of the missing material(s).

At step S404, the method 400 may include computing an initial matrix A' and an initial vector b' to be used in computing the initial vector $\phi'$ for the plurality of transducer locations, wherein A'$\phi'$=b', and wherein each initial vector b' is based on the boundary conditions for each respective transducer location. The initial matrix A' and initial vector b' may be computed based on the initial model of the subject generated in step S402. This results in an initial matrix A' that is easier to solve for than matrix A (e.g., takes less computational time).

By first solving for the initial vector $\phi'$ using the initial matrix A', the method 400 provides a closer initial estimate for input to the optimization algorithm, thereby reducing the total amount of time to solve for $ and select one or more transducer locations.

FIG. 4B depicts an example method 450 for computing an initial estimate (e.g., initial vector $\phi'$) for each transducer location based on an initial model of the subject that is missing all types of material (e.g., tissue, gel, ceramic, polymer, other parts of the transducer, etc.) that are not perfect conductors compared to the model of the subject. This represents an exemplary implementation of the method 400 described in FIG. 4A. The example method 450 may be used to accomplish steps S104 and S106 in the method 100A/100B of FIG. 1A/1B. While an order of operations is indicated in FIG. 4B for illustrative purposes, the timing and ordering of such operations may vary where appropriate without negating the purpose and advantages of the examples set forth in detail herein.

At step S452, the method 450 may include generating an initial model of the subject that is missing all types of material compared to the model of the subject, except for the electrode elements located in three-dimensional space. That is, the initial model may be generated by taking the model of the subject's body and changing the values in the voxels associated with all tissues, ceramic, polymer, gel, and other materials located between the oppositely positioned electrode elements to zero. As such, generating the initial model includes removing everything that is not a perfect (or near-perfect) conductor to obtain a set of perfect conductors suspended in mid-air. In this medium (e.g., air), the solution to A'$\phi'$=b' can be determined by a simple formula for each voxel.

At step S454, the method 450 may include computing an initial estimate ($\phi'$) of electrical potentials in each voxel based on the sign of the voltage that each electrode element is charged with and the distance of the voxel from each electrode element. This provides an approximation ($\phi'$) of the solution in an air-only medium.

By first solving for the initial vector $\phi'$ using distances and charges of the electrode elements compared to each voxel, the method 450 may provide a closer initial estimate for input to the optimization algorithm, thereby reducing the total amount of time to solve for $ and select one or more transducer locations.

FIGS. 5A and 5B depict results of different simulations showing the electrical potentials at a transducer location of a subject's head. FIG. 5A depicts a simulation of the electrical potentials ($\phi$) computed by solving Equation (2), using the model of the subject without any tissue removed. This represents the results, for example, of step S110 of FIG. 1A but with an initial estimate for the initial vector $\phi'$ using a previous technique. FIG. 5B depicts a simulation of the electrical potentials ($\phi'$) computed by solving Equation (1), using an initial vector $\phi'$ that was computed from initial models having all types of materials removed excepted for electrode elements. FIG. 5B represents the results, for example, of step S454 of FIG. 4B. As such, the simulation results shown in FIG. 5B represent an initial vector $\phi'$ (initial estimate) to be used to solve Equation (2) and reach the results of FIG. 5A more quickly.

Table 1 provides results of computing the electrical potentials ($\phi$) associated with a transducer location using step S110 of FIG. 1A based on an initial estimate ($\phi'$) computed using various methods described above. Table 1 also includes results of a previous method for solving equation (2) without first computing an initial estimate ($\phi'$) as a "warm start" for the optimization.

TABLE 1

|  | Previous method | Using method of FIG. 4B | Using method of FIG. 2 using nearest neighbor interpolation | Using method of FIG. 2 using linear interpolation |
|---|---|---|---|---|
| Total computation time (seconds) | 100.17 | 58.438 | 42.067 | 40.293 |

As shown in Table 1, computing the electrical potentials ($\phi$) associated with a transducer location takes approximately 100.17 seconds according to the previous method. Computing the initial estimate ($\phi'$) according to the method of FIG. 4B (removing all material that is not a perfect conductor) and then computing the electrical potentials ($\phi$) using the computed initial estimate takes a total of approximately 58.438 seconds. This is less than 60% of the time for the previous method, indicating good computational time savings. Computing the initial estimate ($\phi'$) according to the method of FIG. 2 (using n=2 for down-sampling and a nearest neighbor interpolation scheme for up-sampling) and then computing the electrical potentials ($\phi$) using the computed initial estimate takes a total of approximately 42.067 seconds. Computing the initial estimate ($\phi'$) according to the method of FIG. 2 (using n=2 for down-sampling and a linear interpolation scheme for up-sampling) and then computing the electrical potentials ($\phi$) using the computed initial estimate takes a total of approximately 40.293 seconds. As such computing the electrical potentials ($\phi$) using the initial estimate computed via the method 200 of FIG. 2 was shown to take only approximately 40% of the time as the previous method, indicating good computational time savings.

FIG. 6 depicts an example method 600 for computing an initial estimate (e.g., initial vector φ') based on a generic model. Steps S608 and S610 of this example method 600 may be used to accomplish step S106 in the method 100A/100B of FIG. 1A/1B. Steps S602-S606 may be performed once for a given generic model, and the solution to step S606 may be saved in memory for use in performing the method 100A/100B of FIG. 1A/1B for any given subject. While an order of operations is indicated in FIG. 6 for illustrative purposes, the timing and ordering of such operations may vary where appropriate without negating the purpose and advantages of the examples set forth in detail herein.

At step S602, the method 600 may include obtaining a generic model that represents a same region of a body as the model of the subject. As an example, the generic model and the model of the subject may both represent a head or brain. The generic model of the head or brain may include, for example, the Colin-27 Average Brain, Stereotaxic Registration Model. As another example, the generic model and the model of the subject may both represent a torso.

At step S604, the method 600 may include computing a matrix A" and a vector b" for the generic model to be used in computing a vector φ". The matrix A" may represent one or more types of tissue, estimated tissue conductivity, and/or other features located in the voxels of the generic model. The b" vector may be computed based on the boundary conditions for each respective transducer location, at locations within the generic model.

At step S606, the method 600 may include computing the vector φ" for each respective transducer location. Specifically, the vector φ" for each transducer location may be computed by computationally solving Equation (3) above. It should be noted that the vector φ" may be determined in other ways than computationally solving a system of equations. The vector φ" for each transducer location may be saved in memory as representing the solution for electrical potentials taken with respect to the generic model. Steps S602-S606 may be performed only one time as the "true solution" for the generic model (e.g., an average brain or torso). Then, the solution (φ") for the generic model may be used to determine φ' for various different subjects using steps S608 and S610 described below. For example, after the solution for the generic model is calculated, this solution may be received or accessed as the first step in the method 600, and the method proceeds to step S608.

At step S608, the method 600 may include determining an affine mapping between the generic model and the model of the subject. This may involve determining an affine transformation from the generic model to the model of the subject based on landmarks, etc., detected from the image data used to obtain the model of the subject.

At step S610, the method 600 may include computing an initial vector φ' for each respective transducer location by calculating a distortion of the vector φ" based on the mapping between the generic model and the model of the subject determined in step S608. That is, step S610 involves using an inverse of the affine mapping known from the generic model to map the solution φ" of the generic model backwards to an approximate solution φ' for the given subject.

By first solving for the initial vector φ' using the generic model and affine mapping, the method 600 provides a closer initial estimate for input to the optimization algorithm, thereby reducing the total amount of time to solve for the vector φ and select one or more transducer locations.

Exemplary Apparatuses

Figure 8:
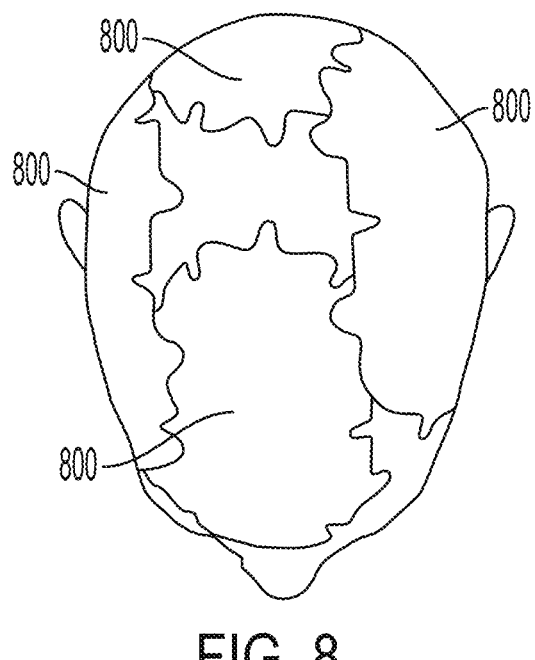
FIG. 8 depicts an example placement of transducers on a subject's head.

FIG. 7 depicts an example apparatus 700 to apply alternating electric fields (e.g., TTFields) to a subject's body. The system may be used for treating a target region of a subject's body with an alternating electric field (e.g., TTFields). As an example, the target region may be in the subject's brain, and an alternating electric field may be delivered to the subject's body via two pairs of transducer arrays positioned on a head of the subject's body (such as, for example, in FIG. 8, which has four transducers 800). As another example, the target region may be in the subject's torso, and an alternating electric field may be delivered to the subject's body via two pairs of transducer arrays positioned on at least one of a thorax, an abdomen, or one or both thighs of the subject's body. Other transducer array placements on the subject's body may be possible.

The example apparatus 700 depicts an example having four transducers (or "transducer arrays") 700A-D. Each transducer 700A-D may include substantially flat electrode elements 702A-D positioned on a substrate 704A-D and electrically and physically connected (e.g., through conductive wiring 706A-D). The substrates 704A-D may include, for example, cloth, foam, flexible plastic, and/or conductive medical gel. Two transducers (e.g., 700A and 700D) may be a first pair of transducers configured to apply an alternating electric field to a target region of the subject's body. The other two transducers (e.g., 700B and 700C) may be a second pair of transducers configured to similarly apply an alternating electric field to the target region.

The transducers 700A-D may be coupled to a voltage generator, such as AC voltage generator 708, and the system may further include a controller 710 communicatively coupled to the AC voltage generator 708. The controller 710 may include a computer having one or more processors 712 and memory 714 accessible by the one or more processors. The memory 714 may store instructions that when executed by the one or more processors control the AC voltage generator 708 to induce alternating electric fields between pairs of the transducers 700A-D according to one or more voltage waveforms and/or cause the computer to perform one or more methods disclosed herein. The controller 710 may monitor operations performed by the AC voltage generator 708 (e.g., via the processor(s) 712). One or more sensor(s) 716 may be coupled to the controller 710 for providing measurement values or other information to the controller 710.

The electrode elements 702A-D may be capacitively coupled. In one example, the electrode elements 702A-D are ceramic electrode elements coupled to each other via conductive wiring 706A-D. When viewed in a direction perpendicular to its face, the ceramic electrode elements may be circular shaped or non-circular shaped. In other embodiments, the array of electrode elements are not capacitively coupled, and there is no dielectric material (such as ceramic, or high dielectric polymer layer) associated with the electrode elements.

The structure of the transducers 700A-D may take many forms. The transducers may be affixed to the subject's body or attached to or incorporated in clothing covering the subject's body. The transducer may include suitable materials for attaching the transducer to the subject's body. For example, the suitable materials may include cloth, foam, flexible plastic, and/or a conductive medical gel. The transducer may be conductive or non-conductive.

The transducer may include any desired number of electrode elements. Various shapes, sizes, and materials may be used for the electrode elements. Any constructions for implementing the transducer (or electric field generating device) for use with embodiments of the invention may be used as long as they are capable of (a) delivering TTFields to the subject's body and (b) being positioned at the locations specified herein. In certain embodiments, at least one electrode element of the first, the second, the third, or the fourth transducer can include at least one ceramic disk that is adapted to generate an alternating electric field. In non-limiting embodiments, at least one electrode element of the first, the second, the third, or the fourth transducer includes a polymer film that is adapted to generate an alternating field.

Figure 9:
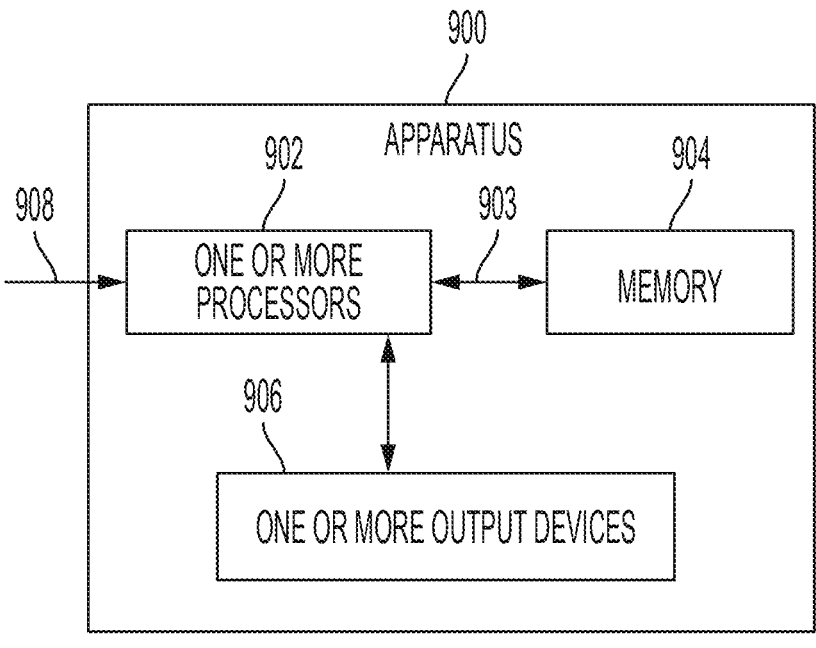
FIG. 9 depicts an example apparatus for performing the disclosed methods.

FIG. 9 depicts an example computer apparatus for use with the embodiments herein. As an example, the apparatus 900 may be a computer to implement certain inventive techniques disclosed herein, such as selecting transducer locations for delivering TTFields to a subject. For example, the steps f FIG. 1A/1B, FIG. 2, FIG. 4, and/or FIG. 6 may be performed by a computer, such as the apparatus 900. As an example, the apparatus 900 may be used as the controller 710 of FIG. 7, or as a separate computer apparatus located remote from the controller 710. The apparatus 900 may include one or more processors 902, memory 904, one or more input devices, and one or more output devices 906.

As one example, based on input 908, the one or more processors 902 generate control signals to control the voltage generator. As an example, the input 908 may be user input. As an example, the input 908 may be from another computer in communication with the apparatus 900. The input 908 may be received in conjunction with one or more input devices (not shown) of the apparatus 900.

The memory 904 may be accessible by the one or more processors 902 (e.g., via a link 903) so that the one or more processors 902 may read information from and write information to the memory 904. The memory 904 may store instructions that when executed by the one or more processors 902 implement one or more methods of the present disclosure.

The one or more output devices 906 may provide the status of the operation of the invention, such as transducer location selection, voltages being generated, and other operational information. The output device(s) 906 may provide visualization data according to certain embodiments of the invention.

The apparatus 900 may be an apparatus for selecting transducer locations for delivering tumor treating fields to a subject, the apparatus including: one or more processors (such as one or more processors 902); and memory (such as memory 904) accessible by the one or more processors, the memory storing instructions that when executed by the one or more processors, cause the apparatus to perform one or more methods described herein.

The memory 904 may be a non-transitory processor readable medium containing a set of instructions thereon for selecting transducer locations for delivering tumor treating fields to a subject, wherein when executed by a processor (such as processor 902), the instructions cause the processor to perform one or more methods described herein.

ILLUSTRATIVE EMBODIMENTS

The invention includes other illustrative embodiments ("Embodiments") as follows.

Embodiment 1: A computer-implemented method for selecting at least one transducer location for delivering tumor treating fields to a subject, the method comprising: obtaining a three-dimensional model of the subject, the model comprising voxels; computing an initial vector $\phi'$ for each of a plurality of transducer locations, wherein each initial vector $\phi'$ represents an initial estimate of electrical potentials for the model for each respective transducer location; computing a matrix A and a vector b, wherein the matrix A is based on the model, wherein the vector b is based on boundary conditions for each respective transducer location; computing a vector $\phi$ using the matrix A, the vector b, and the initial vector $\phi'$ for each transducer location, wherein $A\phi=b$, wherein each vector $\phi$ represents electrical potentials for the model for each respective transducer location; and selecting one or more transducer locations for delivering tumor treating fields to the subject based on the vectors $\phi$.

Embodiment 2: The method of Embodiment 1, wherein computing the vector $\phi$ for each transducer location comprises using an iterative optimizer with the initial vector $\phi'$ for each transducer location.

Embodiment 3: The method of Embodiment 2, wherein the iterative optimizer is a linear equation solver or an algebraic multigrid (AMG) linear solver.

Embodiment 4: The method of Embodiment 1, further comprising computing an initial matrix A' and an initial vector b' to be used in computing the initial vector $\phi'$ for the plurality of transducer locations, wherein $A'\phi'=b'$, wherein each initial vector b' is based on the boundary conditions for each respective transducer location, wherein computing the initial vector $\phi'$ for each transducer location uses the initial matrix A' and the initial vector b' for each transducer location.

Embodiment 5: The method of Embodiment 1, wherein the initial vector $\phi'$ for each transducer location is computed based on a down-sampled model of the subject, wherein the model is down-sampled by using every $n^{th}$ voxel of the model to obtain the down-sampled model of the subject.

Embodiment 6: The method of Embodiment 5, wherein the initial vector $\phi'$ for each transducer location is computed based on an interpolated vector $\phi''$ obtained by solving $A''\phi''=b''$ for each transducer location of the down-sampled model of the subject.

Embodiment 7: The method of Embodiment 1, further comprising: computing a down-sampled model of the subject, wherein the model is down-sampled by using every $n^{th}$ voxel of the model to obtain the down-sampled model of the subject; computing a matrix A" and vectors b" for the down-sampled model, wherein each vector b" is based on the boundary conditions for each respective transducer location; computing a vector $\phi''$ by computationally solving $A''\phi''=b''$ for each respective transducer location; and computing the initial vector $\phi'$ for respective transducer location by up-sampling the vector $\phi''$.

Embodiment 8: The method of Embodiment 7, wherein the initial vector $\phi''$ is up-sampled by interpolating the vector $\phi''$ using one of nearest neighbor interpolation, linear interpolation, b-spline interpolation, Gaussian interpolation, label Gaussian interpolation, zero order interpolation, SciPy nearest interpolation, SciPy linear interpolation, or quadratic interpolation.

Embodiment 9: The method of Embodiment 1, wherein the initial vector $\phi'$ is computed based on an initial model of the subject that is missing at least one type of material compared to the model of the subject.

Embodiment 10: The method of Embodiment 9, wherein the initial model of the subject is missing all types of material except electrode elements compared to the model of the subject.

Embodiment 11: The method of Embodiment 10, wherein the initial vector $\phi'$ is computed based on the sign of voltage that each electrode element is charged with and the distance of each voxel from each electrode element in the initial model.

Embodiment 12: The method of Embodiment 9, wherein the initial model of the subject is missing brain tissue compared to the model of the subject.

Embodiment 13: The method of Embodiment 1, further comprising computing an initial matrix A' and an initial vector b' to be used in computing the initial vector $\phi'$ for the plurality of transducer locations, wherein A'$\phi'$=b', wherein each initial vector b' is based on the boundary conditions for each respective transducer location, wherein the initial matrix A' and the initial vector b' are based on an initial model of the subject that is missing at least one type of material compared to the model of the subject, wherein computing the initial vector $\phi'$ for each transducer location uses the initial matrix A' and the initial vector b' for each transducer location.

Embodiment 14: The method of Embodiment 1, wherein the initial vector $\phi'$ is computed based on a generic model.

Embodiment 15: The method of Embodiment 14, wherein the generic model represents a same region of a body as the model of the subject.

Embodiment 16: The method of Embodiment 15, wherein the generic model and the model of the subject represent a head.

Embodiment 17: The method of Embodiment 14, wherein the generic model and the model of the subject represent a torso.

Embodiment 18: The method of Embodiment 1, further comprising: obtaining a generic model, wherein the generic model represents a same region of a body as the model of the subject; computing a matrix A" and vectors b" for the generic model, wherein each vector b" is based on the boundary conditions for each respective transducer location; computing a vector $\phi"$ by computationally solving A"$\phi"$=b" for each respective transducer location; determining a mapping between the generic model and the model of the subject; and computing the initial vector $\phi'$ for respective transducer locations by calculating a distortion of the vector $\phi"$ based on the mapping between the generic model and the model of the subject.

Embodiment 19: The method of Embodiment 1, further comprising computing at least one of electric power loss density, current density, or electric field intensity at locations of the model of the subject using the vectors $\phi$ for each transducer location, wherein the one or more transducer locations are selected based on the computed electric power loss density, computed current density, or computed electric field intensity.

Embodiment 20: The method of Embodiment 1, further comprising displaying a representation of a selected transducer location on a representation of the subject.

Embodiment 21: The method of Embodiment 1, further comprising displaying at least two selected transducer locations.

Embodiment 22: The method of Embodiment 1, wherein the model of the subject represents a head of the subject.

Embodiment 23: The method of Embodiment 1, wherein the model of the subject represents a torso of the subject.

Embodiment 24: The method of Embodiment 1, wherein each transducer location comprises locations for two pairs of transducers.

Embodiment 25: The method of Embodiment 24, wherein a first pair of the two pairs of transducers has a first transducer and a second transducer, wherein the first transducer and the second transducer are located on opposite sides of the subject.

Embodiment 26: The method of Embodiment 25, wherein a second pair of the two pairs of transducers has a third transducer and a fourth transducer, wherein the third transducer and the fourth transducer are located on opposite sides of the subject.

Embodiment 27: The method of Embodiment 1, wherein each transducer location comprises locations for at least two transducer arrays, wherein each transducer array comprises a plurality of electrode elements.

Embodiment 28: The method of Embodiment 27, wherein the electrode elements are capacitively coupled.

Embodiment 29: The method of Embodiment 27, wherein the electrode elements are not capacitively coupled.

Embodiment 30: The method of Embodiment 27, wherein the electrode elements comprise polymer films.

Embodiment 31: The method of Embodiment 27, wherein the electrode elements comprise ceramic disks.

Embodiment 32: An apparatus for selecting transducer locations for delivering tumor treating fields to a subject, the apparatus comprising: one or more processors; and memory accessible by the one or more processors, the memory storing instructions that when executed by the one or more processors, cause the apparatus to: obtain a three-dimensional model of the subject, the model comprising voxels; compute an initial vector $\phi'$ for each of a plurality of transducer locations, wherein each initial vector $\phi'$ represents an initial estimate of electrical potentials for the model for each respective transducer location; compute a matrix A and a vector b, wherein the matrix A is based on the model, wherein the vector b is based on boundary conditions for each respective transducer location; compute a vector $\phi$ using the matrix A, the vector b, and the initial vector $\phi'$ for each transducer location, wherein A$\phi$=b, wherein each vector $\phi$ represents electrical potentials for the model for each respective transducer location; compute at least one of electric power loss density, current density, or electric field intensity at locations of the model of the subject using the vectors $\phi$ for each transducer location; and select one or more transducer locations based on the computed electric power loss density, computed current density, or computed electric field intensity.

Embodiment 33: The apparatus of Embodiment 32, wherein computing the vector $\phi$ for each transducer location comprises using an iterative optimizer with the initial vector $\phi'$ for each transducer location.

Embodiment 34: The apparatus of Embodiment 32, wherein the initial vector $\phi'$ for each transducer location is computed based on a down-sampled model of the subject.

Embodiment 35: The apparatus of Embodiment 32, wherein the initial vector $\phi'$ for each transducer location is computed based on an initial model of the subject that is missing at least one type of material compared to the model of the subject.

Embodiment 36: The apparatus of Embodiment 32, wherein the initial vector $\phi'$ for each transducer location is computed based on a generic model.

Embodiment 37: A computer-implemented method for computing a dosage of tumor treating fields delivered to a subject, the method comprising: obtaining a three-dimensional model of the subject, the model comprising voxels; computing an initial vector $\phi'$ for a transducer location, wherein the initial vector $\phi'$ represents an initial estimate of electrical potentials for the model for the transducer location; computing a matrix A and a vector b, wherein the matrix A is based on the model, wherein the vector b is based on boundary conditions for the transducer location; computing a vector $\phi$ using the matrix A, the vector b, and the initial vector $\phi'$ for the transducer location, wherein $A\phi=b$, wherein the vector $\phi$ represents electrical potentials for the model for the transducer location; and computing a dosage of tumor treating fields delivered to the subject based on the vector $\phi$.

Embodiment 38: The method of Embodiment 37, further comprising computing at least one of electric power loss density, current density, or electric field intensity at the locations of the model of the subject using the vector $\phi$, wherein computing the dosage is based on at least one of the computed electric power loss density, computed current density, or computed electric field intensity.

Embodiment 39: The method of Embodiment 37, wherein the dosage is at least one of computed local minimum field intensity or computed minimum field power density.

Embodiment 40: A computer-implemented method for selecting at least one transducer location for delivering tumor treating fields to a subject, the method comprising: obtaining a three-dimensional model of the subject, the model comprising voxels; computing an initial vector $\phi'$ for each of a plurality of transducer locations, wherein each initial vector $\phi'$ represents an initial estimate of electrical potentials for the model for each respective transducer location; selecting a subset of transducer locations from the plurality of transducer locations based on the initial vector $\phi'$ computed for each of the plurality of transducer locations; computing a matrix A and a vector b, wherein the matrix A is based on the model, wherein the vector b is based on boundary conditions for each transducer location in the subset of transducer locations; computing a vector $\phi$ using the matrix A and the vector b for each transducer location in the subset of transducer locations, wherein $A\phi=b$, wherein each vector $\phi$ represents electrical potentials for the model for each respective transducer location in the subset of transducer locations; and selecting one or more transducer locations for delivering tumor treating fields to the subject based on the vectors $\phi$.

Embodiments illustrated under any heading or in any portion of the disclosure may be combined with embodiments illustrated under the same or any other heading or other portion of the disclosure unless otherwise indicated herein or otherwise clearly contradicted by context. For example, and without limitation, embodiments described in dependent claim format for a given embodiment (e.g., the given embodiment described in independent claim format) may be combined with other embodiments (described in independent or dependent claim format).

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

What is claimed is:

1. A computer-implemented method for selecting at least one transducer location for delivering tumor treating fields to a subject, the method comprising:
   obtaining a three-dimensional model of the subject, the model comprising voxels;
   computing a subject-specific initial vector $\phi'$ for each of a plurality of transducer locations and for use as an initial estimate for a vector $\phi$ in iteratively solving a system of linear equations $A\phi=b$, wherein each initial vector $\phi'$ represents a subject-specific initial estimate of electrical potentials for the model for each respective transducer location;
   computing the matrix A and the vector b, wherein the matrix A is based on the model, wherein the vector b is based on boundary conditions for each respective transducer location;
   computing the vector $\phi$ for each transducer location and using the matrix A, the vector b for each transducer location, and the initial vector $\phi'$ for each transducer location and by iteratively solving the system of linear equations $A\phi=b$ using the initial vector $\phi'$ as the initial estimate for the vector $\phi$, wherein each vector $\phi$ represents electrical potentials for the model for each respective transducer location; and
   selecting one or more transducer locations for delivering tumor treating fields to the subject based on the vectors $\phi$.

2. The method of claim 1, wherein computing the vector $\phi$ for each transducer location comprises using an iterative optimizer with the initial vector $\phi'$ for each transducer location.

3. The method of claim 2, wherein the iterative optimizer is a linear equation solver or an algebraic multigrid (AMG) linear solver.

4. The method of claim 1, further comprising computing an initial matrix A' and an initial vector b' to be used in computing the initial vector $\phi'$ for the plurality of transducer locations,
   wherein $A'\phi'=b'$,
   wherein each initial vector b' is based on the boundary conditions for each respective transducer location,
   wherein computing the initial vector $\phi'$ for each transducer location uses the initial matrix A' and the initial vector b' for each transducer location.

5. The method of claim 1, wherein the initial vector $\phi'$ for each transducer location is computed based on a down-sampled model of the subject, wherein the model is down-sampled by using every $n^{th}$ voxel of the model to obtain the down-sampled model of the subject.

6. The method of claim 5, wherein the initial vector $\phi'$ for each transducer location is computed based on an interpolated vector $\phi''$ obtained by solving $A''\phi''=b''$ for each transducer location of the down-sampled model of the subject.

7. The method of claim 1, further comprising:
   computing a down-sampled model of the subject, wherein the model is down-sampled by using every $n^{th}$ voxel of the model to obtain the down-sampled model of the subject;
   computing a matrix A'' and vectors b'' for the down-sampled model, wherein each vector b'' is based on the boundary conditions for each respective transducer location;
   computing a vector $\phi''$ by computationally solving $A''\phi''=b''$ for each respective transducer location; and
   computing the initial vector $\phi'$ for respective transducer location by up-sampling the vector $\phi''$.

8. The method of claim 1, wherein the initial vector $\phi'$ is computed based on an initial model of the subject that is missing at least one type of material compared to the model of the subject.

9. The method of claim 8, wherein the initial model of the subject is missing all types of material except electrode elements compared to the model of the subject.

10. The method of claim 1, wherein the initial vector $\phi'$ is computed based on a generic model.

11. The method of claim 10, wherein the generic model represents a same region of a body as the model of the subject.

12. The method of claim 1, further comprising computing at least one of electric power loss density, current density, or electric field intensity at locations of the model of the subject using the vectors $\phi$ for each transducer location, wherein the one or more transducer locations are selected based on the computed electric power loss density, computed current density, or computed electric field intensity.

13. The method of claim 1, further comprising displaying a representation of a selected transducer location on a representation of the subject.

14. The method of claim 1, wherein each transducer location comprises locations for at least two transducer arrays, wherein each transducer array comprises a plurality of electrode elements.

15. An apparatus for selecting transducer locations for delivering tumor treating fields to a subject, the apparatus comprising: one or more processors; and memory accessible by the one or more processors, the memory storing instructions that when executed by the one or more processors, cause the apparatus to:

obtain a three-dimensional model of the subject, the model comprising voxels;

compute a subject-specific initial vector $\phi'$ for each of a plurality of transducer locations and for use as an initial estimate for a vector $\phi$ in iteratively solving a system of linear equations $A\phi=b$, wherein each initial vector $\phi'$ represents a subject-specific initial estimate of electrical potentials for the model for each respective transducer location;

compute the matrix A and the vector b, wherein the matrix A is based on the model, wherein the vector b is based on boundary conditions for each respective transducer location;

compute the vector $\phi$ for each transducer location and using the matrix A, the vector b for each transducer location, and the initial vector $\phi'$ for each transducer location and by iteratively solving the system of linear equations $A\phi=b$ using the initial vector $\phi'$ as the initial estimate for the vector $\phi$, wherein each vector $\phi$ represents electrical potentials for the model for each respective transducer location;

compute at least one of electric power loss density, current density, or electric field intensity at locations of the model of the subject using the vectors $\phi$ for each transducer location; and select one or more transducer locations based on the computed electric power loss density, computed current density, or computed electric field intensity.

16. The apparatus of claim 15, wherein computing the vector $\phi$ for each transducer location comprises using an iterative optimizer with the initial vector $\phi'$ for each transducer location.

17. The apparatus of claim 15, wherein the initial vector $\phi'$ for each transducer location is computed based on a down-sampled model of the subject.

18. The apparatus of claim 15, wherein the initial vector $\phi'$ for each transducer location is computed based on an initial model of the subject that is missing at least one type of material compared to the model of the subject.

19. The apparatus of claim 15, wherein the initial vector $\phi'$ for each transducer location is computed based on a generic model.

20. A computer-implemented method for computing a dosage of tumor treating fields delivered to a subject, the method comprising:

obtaining a three-dimensional model of the subject, the model comprising voxels;

computing a subject-specific initial vector $\phi'$ for a transducer location and for use as an initial estimate for a vector $\phi$ in iteratively solving a system of linear equations $A\phi=b$, wherein the initial vector $\phi'$ represents a subject-specific initial estimate of electrical potentials for the model for the transducer location;

computing the matrix A and the vector b, wherein the matrix A is based on the model, wherein the vector b is based on boundary conditions for the transducer location;

computing the vector $\phi$ for the transducer location and using the matrix A, the vector b for the transducer location, and the initial vector $\phi'$ for the transducer location and by iteratively solving the system of linear equations $A\phi=b$ using the initial vector $\phi'$ as the initial estimate for the vector $\phi$, wherein the vector $\phi$ represents electrical potentials for the model for the transducer location; and computing a dosage of tumor treating fields delivered to the subject based on the vector $\phi$ for the transducer location.

* * * * *